United States Patent [19]
Jung

[11] Patent Number: 5,930,858
[45] Date of Patent: Aug. 3, 1999

[54] TOOTHBRUSH AND METHOD OF SIGNALING THE LENGTH OF BRUSHING TIME

[75] Inventor: Philipp Jung, Darmstadt, Germany

[73] Assignee: Braun Aktiengesellschaft, Frankfurt, Germany

[21] Appl. No.: 08/811,508

[22] Filed: Mar. 4, 1997

Related U.S. Application Data

[63] Continuation of application No. PCT/EP95/04046, Oct. 14, 1995, abandoned.

[30]  Foreign Application Priority Data

Nov. 8, 1994 [DE] Germany ............................. 44 39 835

[51] Int. Cl.⁶ ................................................... A46B 13/02
[52] U.S. Cl. .............................................. 15/22.1; 368/10
[58] Field of Search ....................... 15/22.1, 105, 167.1; 368/10, 230, 248

[56]  References Cited

U.S. PATENT DOCUMENTS

| | | | |
|---|---|---|---|
| 4,450,599 | 5/1984 | Scheller et al. ........................... | 15/22.1 |
| 5,089,998 | 2/1992 | Rund ....................................... | 368/230 |
| 5,559,761 | 9/1996 | Frenkel ................................... | 368/230 |
| 5,561,881 | 10/1996 | Klinger et al. ............................ | 15/105 |
| 5,704,087 | 1/1998 | Strub ....................................... | 15/105 |

FOREIGN PATENT DOCUMENTS

| | | | |
|---|---|---|---|
| 210094 | 1/1987 | European Pat. Off. ............... | 15/167.1 |
| 31 17 160 | 11/1982 | Germany . | |
| 33 09 687 | 9/1984 | Germany . | |
| 3309687 | 9/1984 | Germany ............................. | 15/167.1 |
| 34 33 250 | 3/1986 | Germany . | |
| 40 29 770 | 3/1992 | Germany . | |
| 4322604 | 12/1992 | Japan . | |
| 2 243 569 | 11/1991 | United Kingdom . | |
| 2 252 234 | 8/1992 | United Kingdom . | |
| 2252234 | 8/1992 | United Kingdom ..................... | 15/105 |

OTHER PUBLICATIONS

Copy of International Search Report dated Jan. 18, 1996.

*Primary Examiner*—Terrence R. Till
*Attorney, Agent, or Firm*—Fish & Richardson P.C.

[57]  ABSTRACT

The invention is directed to a method and an electric toothbrush which includes a timing circuit (7) serving to signal to a user the expiration of a first period (T1), that is, the expiration of the optimum brushing time, following activation of the electric toothbrush. Further, an On/Off switching device (4) is provided which is controllable by the timing circuit (7) and by means of which the electric toothbrush can be turned on and off. The timing circuit (7) controls the On/Off switching go0 device (4) such that following expiration of the first period (T1) the electric toothbrush is turned on and off repeatedly within a second period (T2). As a result, the user of the electric toothbrush "senses" directly the end of the first period (T1), that is, the end of the optimum brushing time, from the variation in the operating mode of the electric toothbrush.

14 Claims, 2 Drawing Sheets

TOOTHBRUSH AND METHOD OF SIGNALING THE LENGTH OF BRUSHING TIME

This application is a continuation of International Application No. PCT/EP95/04046, filed Oct. 14, 1995, now abandoned, which claims the benefit of German Application Serial No. P 44 39 835.2, filed Nov. 8, 1994.

BACKGROUND OF THE INVENTION

This invention relates to an electric toothbrush having a timing circuit serving to signal to a user the expiration of a first period following activation of the electric toothbrush, with an On/Off switching device being provided which is controllable by the timing circuit and with which the electric toothbrush can be turned on and off.

BRIEF SUMMARY OF THE INVENTION

A toothbrush of this type is known from German Offenlegungsschrift DE 33 09 687 A1. In this specification, a time switch is provided which, based upon the instant the electric toothbrush is activated, emits user-perceivable signals following expiration of a predetermined length of time. The signals serve the function of indicating to the user the end of the brushing time. The signals involved are audible and/or visual signals intended to inform the user that the optimum brushing time has elapsed. Further, the specification describes that the electric toothbrush can be turned off simply automatically upon expiration of the predetermined period.

It is an object of the present invention to provide an electric toothbrush which is further improved in respect of the signaling that the brushing time has expired.

According to the present invention, this object is accomplished in an electric toothbrush of the type initially referred to in that the timing circuit controls the On/Off switching device such that following expiration of the first period the electric toothbrush is turned on and off repeatedly within a second period.

Following expiration of the first period, that is, for example, at the end of the total brushing time or the brushing time for a particular area of the teeth, the electric toothbrush is turned off and turned on again repeatedly, in particular at short intervals. These actions of turning on and off are maintained for the length of the second period. Hence, the electric toothbrush is caused to switch from a uniform On mode to a non-uniform intermittent mode. A user becomes aware of this transistion directly by reason of the changed vibrations of the handle member and the brush head of the electric toothbrush. The user thus recognizes the end of the brushing time solely from the variation in the operating mode, that is, the predesigned change in vibration of the electric toothbrush or the handle member. Therefore, the user is no longer required to observe an audible or visual signaling means, "sensing" instead the end of the brushing time "in his or her hand and mouth" readily.

Conveniently, the second period is short compared with the first period, that is, the non-uniform intermittent mode lasts a substantially shorter time than the predetermined brushing time. About one to three minutes, preferably two minutes for the first period, that is, the optimum brushing time, and about three to ten seconds for the second period, that is, for the length of time in which the end of the brushing time is signaled, have proven to be advantageous.

Further, it is desirable that an On interval or an Off interval occurring within the second period be short compared with the second period. A period of about 0.5 second has proven to be an advantageous On or off interval.

In an advantageous further feature of the present invention, the timing circuit controls the On/Off switching device such that the first period is restarted following expiration of the second period. Hence, the electric toothbrush automatically returns to the On mode after the brushing time has elapsed as well as following expiration of the period in which the end of the brushing time is signaled. This has the advantage of enabling the user to continue brushing in excess of the predetermined brushing time, if so desired, without any further action, in particular without the need to turn the electric toothbrush on again manually.

In advantageous embodiments of the present invention, the timing circuit is configured as one or several digital inter grated modules, and/or a clock is provided which is coupled to or integrated with the timing circuit, and/or the On/Off switching device is configured as a transistor. As a result, all of the components necessary for implementing the invention can be accommodated in the handle member of the electric toothbrush without difficulty.

In a still further feature of the invention, a further On/Off switch is provided enabling the user to turn the electric toothbrush on, thus starting the first period, and enabling the user to turn the electric toothbrush off as desired. This further On/Off switch may be in particular a mechanical On/Off switch. This switch enables the user to activate the electric toothbrush for use and deactivate it subsequently. The heretofore customary operation of the electric toothbrush is thus maintained unchanged for its user.

The present invention further relates to an advantageous method of signaling the brushing time as well.

Further features, advantages and application possibilities of the present invention will become apparent from the subsequent description of embodiments illustrated in more detail in the accompanying drawings. It will be understood that any single feature and any combination of single features described and/or represented by illustration form the subject-matter of the present invention, irrespective of their summary in the claims and their back-reference.

BRIEF DESCRIPTION OF THE DRAWINGS

In the drawings,

FIG. 4 illustrates an electronic toothbrush 20 in accordance with one embodiment. The electronic toothbrush 20 includes a brush head 22, a handle member 24, and a mechanical On/Off switch 26. The electric toothbrush 20 has uniform On and non-uniform intermittent operating modes, which are described below. A user becomes aware of a transition between uniform On and non-uniform intermittent modes of operation through changed vibrations of the handle member 24 and/or the brush head 22.

DETAILED DESCRIPTION OF THE INVENTION

Figure 1:
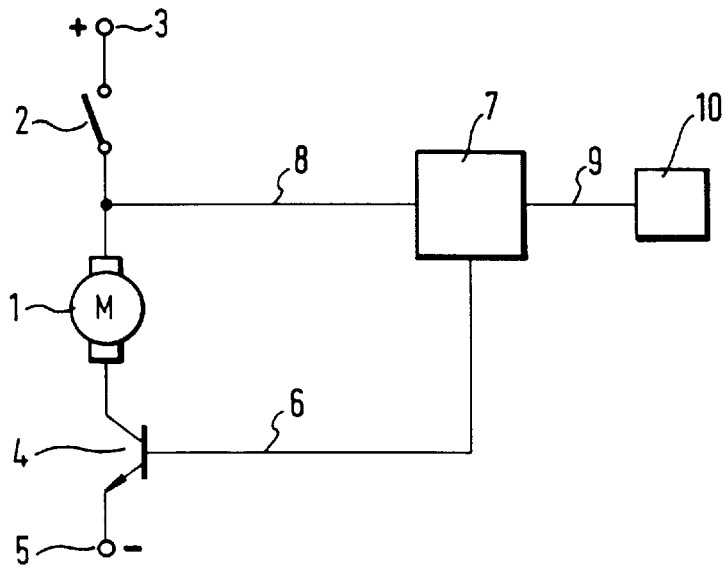
FIG. 1 is a schematic circuit diagram of an electric drive mechanism with an associated drive control means for an electric toothbrush according to the present invention.

Referring now to FIG. 1 of the drawings, there is shown an electric motor 1 for an electric toothbrush, which motor is connected by means of an in particular mechanical On/Off switch 2 to the positive terminal 3 of a source of electric power, in particular a storage battery, and which is connected by means of an in particular electronic On/Off switching device 4, preferably a transistor or a power transistor, to the negative terminal 5 of the power source identified. The On/Off switch 2 is actuated by a user and serves to turn the electric toothbrush on and off. The On/Off switching device 4 is controlled via a line 6 by a timing circuit 7. In cases where a transistor is used as On/Off switching device 4, the line 6 is connected to the base of the transistor.

A line 8 connects the timing circuit 7 to a node between the electric motor 1 and the On/Off switch 2. Further, a line 9 connects the timing circuit 7 to a clock 10. The clock 10 generates a uniform pulse at periodic intervals passed on via the line 9 to the timing circuit 7 and used by the timing circuit 7 as time basis.

Figure 2:
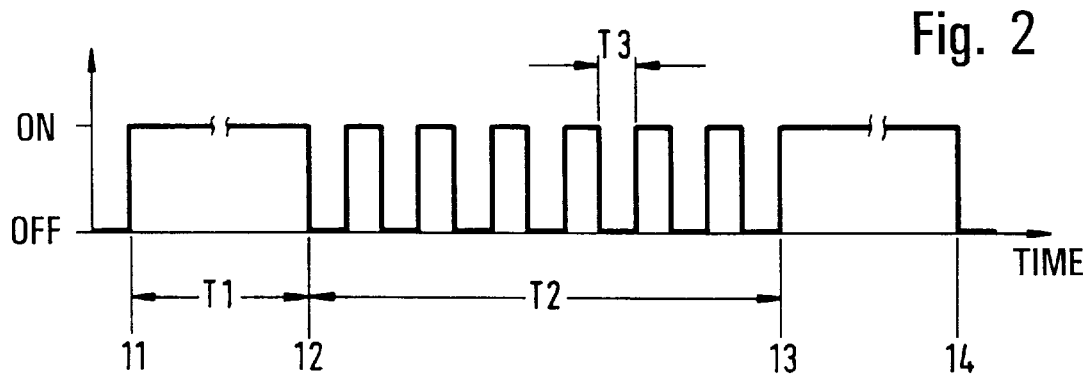
FIG. 2 is a schematic timing chart showing the On and Off operating modes of the electric toothbrush of FIG. 1.

The mode of operation of the electric motor 1 and the associated timing circuit of the electric toothbrush will be explained in the following with reference to FIG. 2. Plotted on the abscissa of the timing chart illustrated in FIG. 2 is the time, while the On and Off operating modes of the electric motor 1 or the electric toothbrush are plotted on the ordinate. The time intervals shown on the abscissa of the timing chart are not to scale.

At an instant of time 11, the electric motor 1 and hence the electric toothbrush are turned on by the user actuating the On/Off switch 2. This is possible because the On/Off switching device 4 is closed, allowing current to flow from the positive terminal 3 through the electric motor 1 to the negative terminal 5.

This On operating mode of the electric toothbrush is maintained for a first period T1 ending at an instant of time 12. The first period T1 thus represents a predetermined brushing time which preferably corresponds to an optimum brushing time. This first period may be set to about two minutes, for example.

On detecting the end of the first period T1, the timing circuit 7 informs the user thereof by varying the mode of operation of the electric toothbrush. To this end, the timing circuit 7 turns the electric motor 1 and hence the electric toothbrush off and on again repeatedly by means of the On/Off switching device 4. These actions of turning the electric toothbrush off and on are maintained by the timing circuit 7 for the length of a second period T2 ending at an instant of time 13. This second period T2 represents the period in which the end of the first period T1, that is, the end of the predetermined brushing time, is signaled to the user by the repeated On and Off actions. This second period T2 is shorter than the first period T1, lasting, for example, between seven and eight seconds, approximately.

The lengths of the On and Off intervals for which the electric toothbrush is turned on and off during the second period T2 are designated by T3. This period T3 is shorter than the second period T2, lasting between 0.3 and 1 second, for example. It will be understood that the On and Off intervals may also be of different lengths.

The timing circuit 7 detects the end of the second period T2, driving again the electric toothbrush into the On operating mode corresponding to the first period T1. In consequence, the On/Off switching device 4 is closed. The user may then continue using the electric toothbrush and has the option of either turning the electric toothbrush off by means of the On/Off switch 2 at an instant of time 14, as shown in FIG. 2, or continuing the use of the electric toothbrush until the expiration of the first period T1 is again signaled in the manner previously described.

Figure 3:
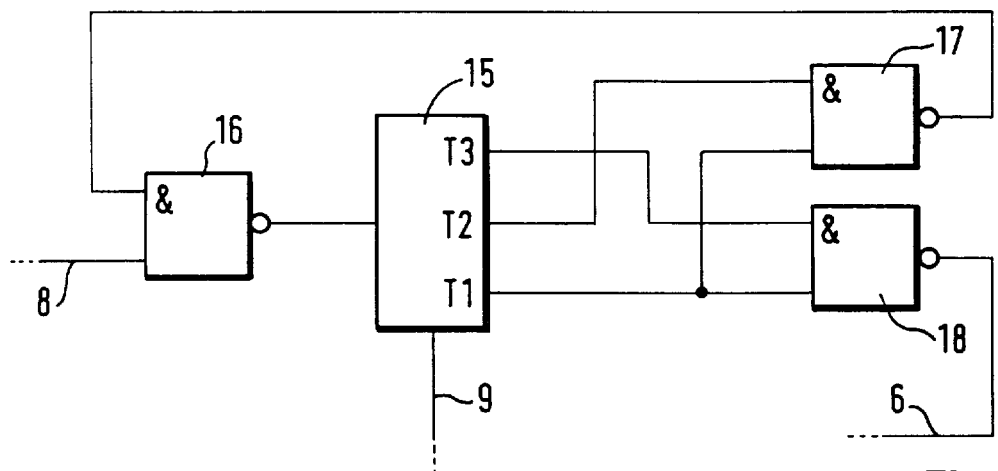
FIG. 3 is a schematic circuit diagram of the drive control means of the electric toothbrush of FIG. 1.
Figure 4:
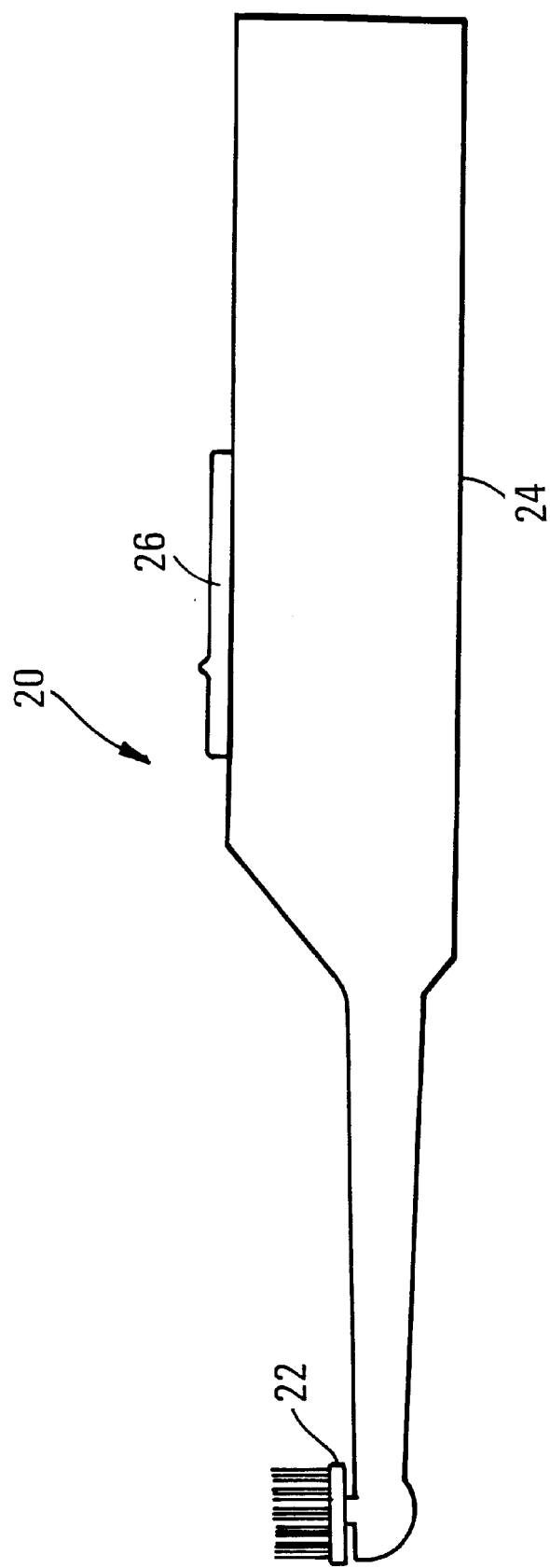
FIG. 4 illustrates one embodiment of an electric toothbrush employing the electric drive mechanism and drive control of FIG. 1.

FIG. 3 illustrates a possible embodiment of the timing circuit 7. An interval timer 15 is connected to the clock 10 via the line 9. Further, the interval timer 15 is connected to the output of a NAND gate 16 having its first input connected via the line 8 to the node between the electric motor 1 and the On/Off switch 2.

The interval timer 15 has three outputs which are associated, respectively, with the first period T1, the second period T2 and the On/Off intervals T3. The output associated with the first period T1 is connected to the first input of two NAND gates 17 and 18, respectively. The output of the interval timer 15 associated with the second period T2 is connected to the second input of the NAND gate 17, while the output of the interval timer 15 associated with the On/Off intervals T3 is connected to the second input of the NAND gate 18. The output of the NAND gate 17 is connected to the second input of the NAND gate 16, and the output of the NAND gate 18 is connected to the line 6 going to the On/Off switching device 4.

In addition, the interval timer 15 is connected to the line 9 leading to the clock 10.

The interval timer 15 is a digital integrated module. The same applies to the NAND gates 16, 17, 18 and the clock 10. In this configuration, it is possible for the interval timer 15 and the clock 10 to be integrated on a module.

When the user turns the electric toothbrush on by means of the On/Off switch 2, the interval timer 15 is started via the NAND gate 16 because of the voltage variation occurring on the line 8. The outputs of the NAND gates 17, 18 are logical highs. As a result, the On/Off switching device 4 is closed. Following expiration of the period T1, the output of the interval timer 15 associated with this particular period goes to a logical high. When the output associated with the On/Off intervals T3 goes equally to a logical high, the output of the NAND gate 18 goes to a logical low. As a result, the electric motor 1 and hence the electric toothbrush are deactivated via the On/Off switching device 4. After the period T3 has elapsed, the associated output of the interval timer 15 goes back to a logical low, causing the electric toothbrush to be turned on again. The electric toothbrush is thus turned on and off in alternating sequence, with the On/Off intervals being each of a length T3. These operations of turning the toothbrush on and off are repeated until the output of the interval timer 15 associated with the period T2 goes to a logical high. As a result, both inputs of the NAND gate 17 are logical highs, the output thus going to a logical low. In this process, the output of the NAND gate 16 is switched to a logical low at least for a short time, causing the interval timer 15 to be restarted. Hence, the period T1 and thus the complete sequence of operations described starts afresh. The user may turn the electric toothbrush off by means of the On/Off switch 2, as mentioned in the foregoing.

The invention claimed is:

1. An electric toothbrush comprising: a brush head, a handle member including a timing circuit (7) to signal to a user the expiration of a first period (T1) following activation of the electric toothbrush; and an On/Off switching device (4) which is controllable by the timing circuit (7) and with which the electric toothbrush can be turned on and off; and characterized in that the timing circuit (7) controls the On/Off switching device (4) such that following expiration of the first period (T1) the electric toothbrush turns on and off repeatedly within a second period (T2).

2. The electric toothbrush as claimed in claim 1, characterized in that the second period (T2) is short compared with the first period (T1).

3. The electric toothbrush as claimed in claim 1 or 2, characterized in that an On interval or an Off interval occurring within the second period (T2) is short compared with the second period (T2).

4. The electric toothbrush of claim 1, characterized in that the first period (T1) lasts between one minute and three minutes, approximately.

5. The electric toothbrush of claim 1, characterized in that the second period (T2) lasts between three and ten seconds, approximately.

6. The electric toothbrush of claim 1, characterized in that the period (T3) of an On or Off interval of the second period (T2) lasts between 0.3 second and one second, approximately.

7. The electric toothbrush of claim 1, characterized in that the timing circuit (7) controls the On/Off switching device (4) such that the first period (T1) is restarted following expiration of the second period (T2).

8. The electric toothbrush of claim 1, characterized in that the timing circuit (7) includes at least one digital integrated module.

9. The electric toothbrush of claim 1, further comprising a clock (10) which is one of coupled to and integrated with the timing circuit (7).

10. The electric toothbrush of claim 1, characterized in that the On/Off switching device (4) includes a transistor to switch On or Off the toothbrush.

11. The electric toothbrush of claim 1, further comprising a mechanical On/Off switch (2) to enable the user to activate the electric toothbrush to start the first period (T1), and to deactivate the electric toothbrush.

12. The electric toothbrush of claim 1, wherein the second period (T2) lasts between about seven and eight seconds.

13. A method of signaling the brushing time with an electronic toothbrush, comprising:

operating the brush in an On mode during a first time period; and then, switching the brush between the On mode and an off mode repeatedly during a second time period, the step of switching being started electronically and automatically in response to the first time period elapsing.

14. The method of claim 12, further comprising:

operating the brush in the On mode for another first time period (T1) in response to the second time period (T2) elapsing, the second step of operating being started electronically and automatically.

\* \* \* \* \*